United States Patent
Romano et al.

[11] Patent Number: 6,024,020
[45] Date of Patent: Feb. 15, 2000

[54] FLUORESCENCE DOT AREA METER FOR MEASURING THE HALFTONE DOT AREA ON A PRINTING PLATE

[75] Inventors: David J. Romano, Lowell; Edward L. Kelley, Lexington, both of Mass.

[73] Assignee: Agfa Corporation, Wilmington, Mass.

[21] Appl. No.: 08/873,135

[22] Filed: Jun. 10, 1997

Related U.S. Application Data

[63] Continuation-in-part of application No. 08/701,028, Aug. 21, 1996, Pat. No. 5,729,348.

[51] Int. Cl.$^7$ .................................................. B41F 33/00
[52] U.S. Cl. ...................... 101/484; 101/456; 250/458.1; 250/205; 356/379; 356/417
[58] Field of Search ................... 101/365, 401.1, 101/467, 483, 484, DIG. 45, DIG. 47, 453, 456; 250/458.1, 459.1, 205; 356/379, 417; 358/298; 382/112

[56] References Cited

U.S. PATENT DOCUMENTS

| | | | |
|---|---|---|---|
| 3,185,088 | 5/1965 | Norton | 101/350.1 |
| 3,636,251 | 1/1972 | Daly et al. | 358/297 |
| 3,958,509 | 5/1976 | Murray et al. | 101/365 |
| 4,131,879 | 12/1978 | Ehrat | 382/135 |
| 4,339,525 | 7/1982 | Bratt et al. | 430/271 |
| 4,395,946 | 8/1983 | Price | 101/152 |
| 4,473,298 | 9/1984 | Sakamoto | 356/432 |
| 4,516,856 | 5/1985 | Popelka | 250/458.1 |
| 4,649,500 | 3/1987 | Yamada et al. | 101/170 |
| 4,649,566 | 3/1987 | Tsunoda et al. | 382/112 |
| 4,665,496 | 5/1987 | Ott | 101/365 |
| 5,033,378 | 7/1991 | Ebihara | 101/DIG. 45 |
| 5,119,132 | 6/1992 | Butler | 250/205 |
| 5,163,368 | 11/1992 | Pensavechia et al. | 101/DIG. 47 |
| 5,339,737 | 8/1994 | Lewis et al. | 101/457 |
| 5,578,818 | 11/1996 | Kain et al. | 250/458.1 |
| 5,724,143 | 3/1998 | Huber et al. | 356/419 |
| 5,729,348 | 3/1998 | Romano | 356/417 |

FOREIGN PATENT DOCUMENTS

| | | | |
|---|---|---|---|
| 0636475 | 2/1995 | European Pat. Off. | |
| 0755781 | 1/1997 | European Pat. Off. | |
| 3444891 | 6/1986 | Germany | 101/DIG. 45 |
| 95145 | 6/1984 | Japan | 101/DIG. 47 |
| 9202368 | 2/1992 | WIPO | |

OTHER PUBLICATIONS

XP-002074944 Romano, A Fluorescence Dot Area Meter, Feb. 10, 1997.

*Primary Examiner*—Stephen R. Funk
*Attorney, Agent, or Firm*—John A. Merecki

[57] ABSTRACT

A fluorescence dot area meter for accurately measuring halftone dot area on a printing plate having an emulsion containing one or more fluorescent compounds. The fluorescent dot area meter generally includes an illumination source for providing light having a first range of wavelengths, a system for exposing the printing plate to this light to cause the printing plate to emit light (fluoresce) within a second, higher range of wavelengths, and a system for determining halftone dot area based on a measurement of the light emitted by the printing plate.

13 Claims, 10 Drawing Sheets

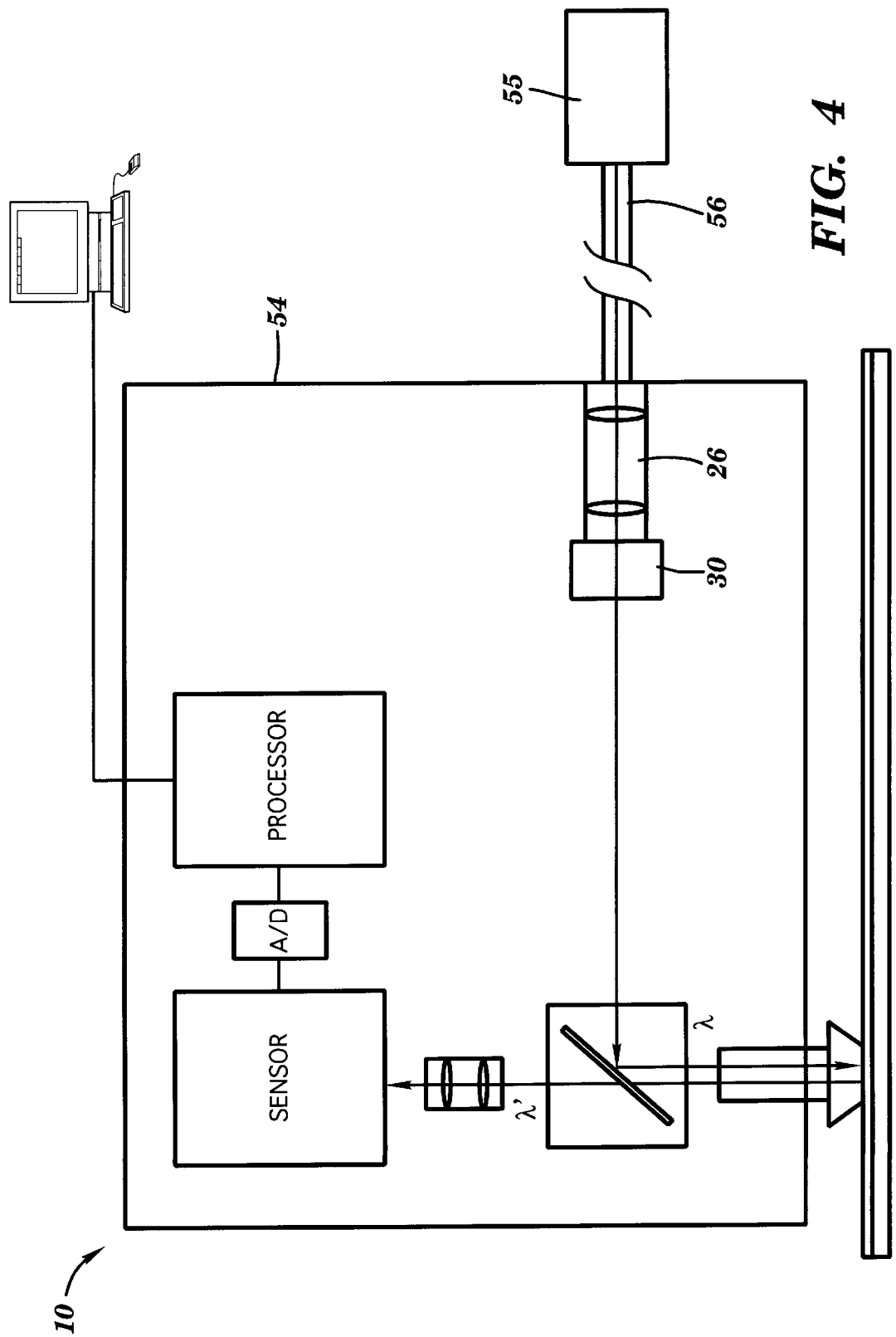

FLUORESCENCE DOT AREA METER FOR MEASURING THE HALFTONE DOT AREA ON A PRINTING PLATE

The present patent application is a continuation-in-part of copending patent application Ser. No.: 08/701,028 filed Aug. 21, 1996, entitled "Fluorescence Dot Area Meter now U.S. Pat. No. 5,729,348."

FIELD OF THE INVENTION

The present invention provides a method and apparatus for accurately measuring halftone dot area on a printing plate having at least one layer containing a fluorescent compound.

BACKGROUND OF THE INVENTION

Reflection densitometers provide an accurate measurement of halftone dot area on prints produced by an output device such as a printing press or the like. Unfortunately, the reflection densitometer has been proven to be unreliable for measuring halftone dot area on printing plates. This is due in part to the reflective directionality of the grain of the printing plate, the lack of image contrast on the printing plate, and the small signal to noise ratio of the measurements provided by a densitometer. Regardless of the cause, a reflection densitometer will typically provide contradictory readings if rotated even slightly over an area of a printing plate being measured. The deficiencies of a reflection densitometer become even more evident when used to measure dot area on a printing plate imaged in a curved state in a direct to press printing system.

SUMMARY OF THE INVENTION

The present invention provides a fluorescence dot area meter for accurately measuring halftone dot area on a printing plate. The fluorescent dot area meter generally includes an illumination source for providing light having a first range of wavelengths, a system for exposing the printing plate to this light to cause the printing plate to emit light (fluoresce) within a higher, second range of wavelengths, and a system for determining halftone dot area based on a measurement of the light emitted by the printing plate.

BRIEF DESCRIPTION OF THE DRAWINGS

The features of the present invention will best be understood from a detailed description of the invention and a preferred embodiment thereof selected for the purposes of illustration and shown in the accompanying drawings in which:

FIG. 4 illustrates a general block diagram of a fluorescence dot area meter utilizing an external illumination source;

DETAILED DESCRIPTION OF THE INVENTION

Figure 1:
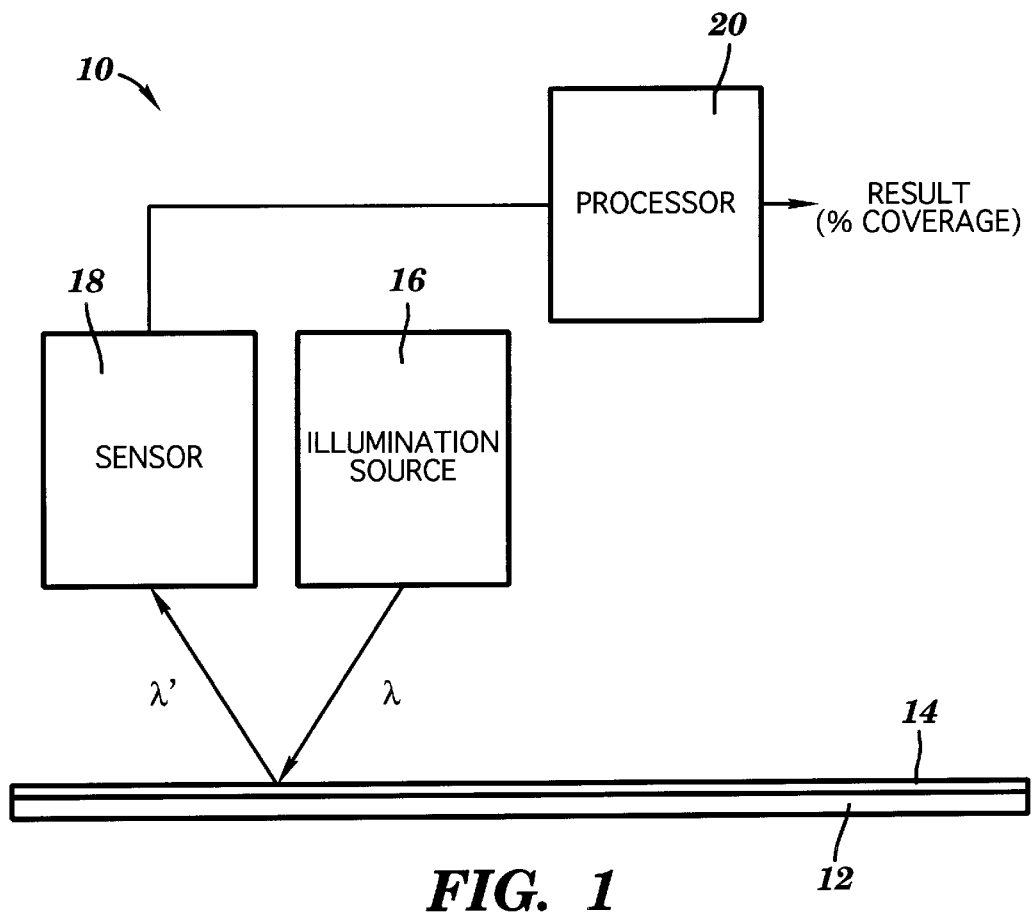
FIG. 1 illustrates a general block diagram of a fluorescence dot area meter in accordance with the present invention.

The objects, features, and advantages of the present invention are illustrated in detail in the accompanying drawings, wherein like reference numerals refer to like elements throughout the drawings.

A general block diagram of a fluorescence dot area meter 10 in accordance with the present invention is illustrated in FIG. 1. The fluorescence dot area meter 10 is used to provide halftone dot area measurements on a printing plate 12 having a surface emulsion 14 and/or other layer which includes one or more fluorescent compounds. As known in the art, the areas of emulsion 14 remaining on the surface of the printing plate 12 after the plate has been recorded and developed correspond to recorded halftone dots.

The fluorescence dot area meter 10 includes an illumination source 16. The illumination source 16 provides light λ having a first range of wavelengths with sufficient energy to cause particular molecules in the emulsion 14 remaining on the surface of the printing plate 12 to become excited enough to emit light λ' within a second, higher range of wavelengths (i.e., to fluoresce). This is illustrated in FIG. 1. Specifically, the printing plate 12 is exposed to the light λ emitted by the illumination source 16, causing the emulsion 14 remaining on the printing plate 12 to emit light λ' within a second, higher range of wavelengths.

The light λ' emitted by a section of the printing plate 12 is isolated and detected by a sensor 18. The output of the sensor 18 is provided to a processor 20 which calculates the percentage of the area within the section of the printing plate 12 that is covered by halftone dots (% coverage). Generally, each section of the printing plate 12 to be measured corresponds to a predetermined halftone test pattern, such as a 50% halftone comprising 8×8 dot pixels. If the dot area measurements output by the processor 20 are not satisfactory, various platemaking variables, such as exposure, focus, and pulse width modulation, can be adjusted as required to optimize the characteristics (e.g., size, shape) of the halftone dots recorded on the printing plate 12.

The fluorescence dot area meter 10 is designed to be used with printing plates 12 having a surface emulsion 14 or other layer containing one or more fluorescent compounds. For example, the fluorescence dot area meter 10 of the present invention can be used to determine halftone dot area measurements on the aluminum N90™ printing plate manufactured by the Agfa Division of Bayer Corporation. Specifically, yellow light in the region of about 540–640 nm, peaking at 570 nm, is emitted by the recorded dots on the aluminum N90™ printing plate when the plate is exposed to blue light in the region of about 450–500 nm. The emitted yellow light can be viewed and measured by filtering out the blue light reflected by the unexposed sections of the plate.

The fluorescence dot area meter 10 calculates dot area using a variation of the well known Yule-Neilsen equation (EQU. 1). As known in the art, the Yule-Neilsen equation is commonly used to determine the dot area on prints using measurements provided by a reflection densitometer. The Yule-Neilsen equation is presented in detail in an article entitled "The Penetration of Light Into Paper and its Effects on Halftone Reproduction" (Yule and Neilsen, TAGA Proceedings, 1951, pp. 65–76), incorporated herein by reference.

$$\% = \frac{1 - 10^{-\frac{(t-p)}{N}}}{1 - 10^{-\frac{(s-p)}{N}}} \times 100 \qquad (EQU.1)$$

Where:
%=Percent of print area covered by halftone dots
t=Density of the halftone tint area
p=Density of the paper or background area
s=Density of the solid or 100% covered area
N=N-factor used to correct for optical effects Since the fluorescence dot area meter 10 measures the amount of emitted light, rather than the absence of light (i.e., density), the Yule-Neilsen equation is simplified:

$$\% = \frac{(t-p)^N}{(s-p)^N} \times 100 \qquad (EQU.2)$$

The purpose of the N-factor in EQU. 1 is to account for light which penetrates the translucent surface of paper, where it becomes trapped under, and is absorbed by, the ink of the halftone dots. This effectively creates a shadow around the dots. Since a reflection densitometer only measures integral densities, it cannot differentiate between a halftone dot and the optically created shadows. This effect, which is commonly referred to as "loptical dot gain," increases the measured dot area. The N-factor in EQU. 1 lowers the measured dot areas to better approximate the real geometric area of the halftone dots.

The fluorescence dot area meter 10 measures halftone dots on the opaque surface of the printing plate 12 by measuring brightness rather than density. As a consequence, the effect of optical dot gain is reversed and becomes "optical dot sharpening." In this case, as presented in EQU. 2, the N-factor is used to increase the dot areas in order to correct for brightness losses due to optical effects and other factors.

The N-factor is determined by first measuring a sample of halftone dots on a printing plate using an image analysis system. This establishes the actual geometric area of the dots. This measurement is then compared to the output of the fluorescence dot area meter 10 for the same sample of halftone dots. The N-factor is adjusted in EQU. 2 until the dot area measurement provided by the meter 10 matches the actual geometric area of the dots as closely as possible.

Figure 2:
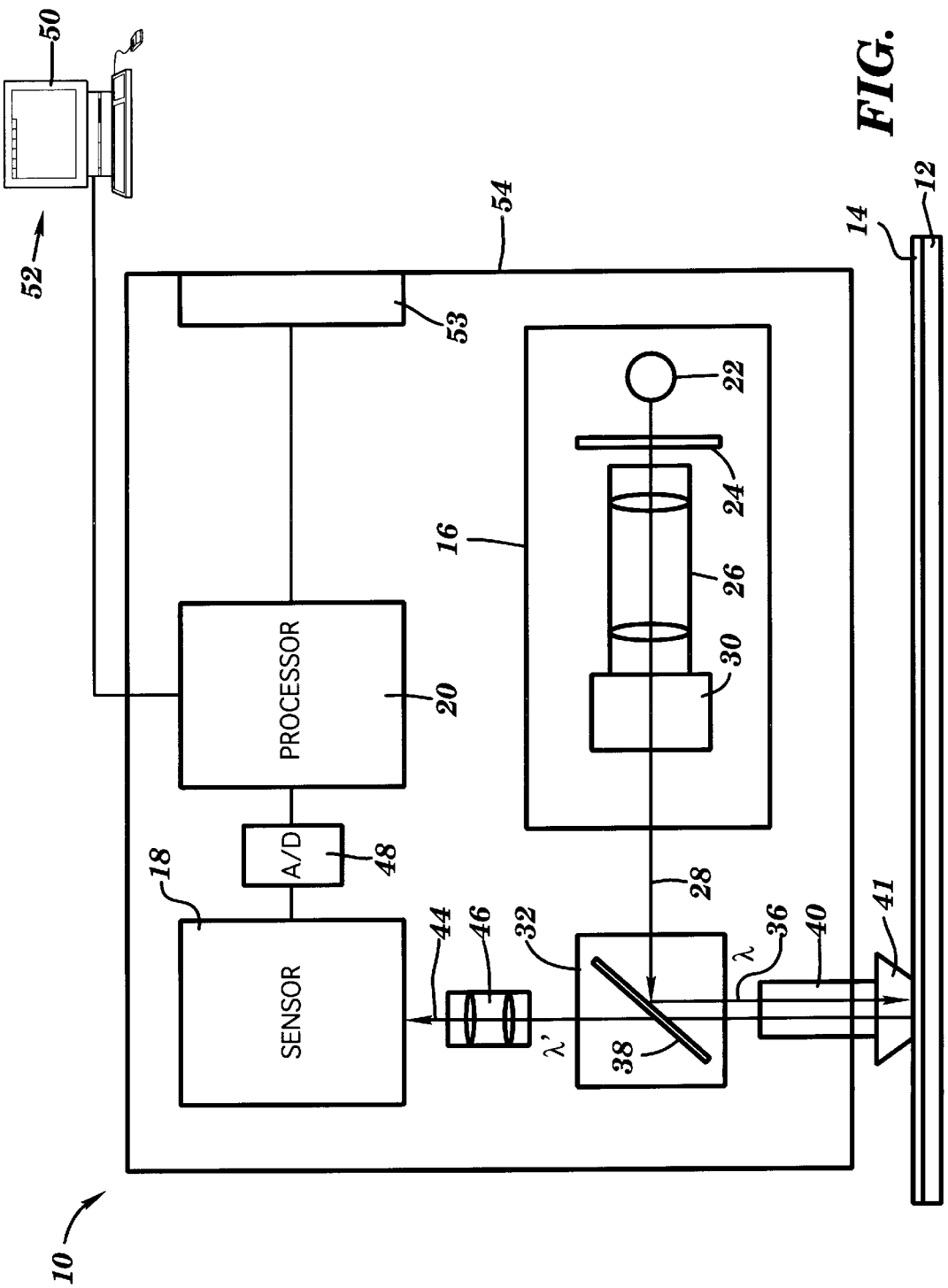
FIG. 2 illustrates in detail a first embodiment of the fluorescence dot area meter.

The fluorescence dot area meter 10 of the present invention is illustrated in greater detail in FIG. 2. As shown, the illumination source 16 comprises a lamp 22, a layer of heat absorbing glass 24, and a collimator 26 for focusing the output of the lamp 22 into a light beam 28. Preferably, a low wattage, high intensity lamp 22 is used, such as a 50–100 W halogen lamp, to prevent excessive heat build up within the meter 10, and to avoid heating or quenching the surface of the printing plate 12. The layer of heat absorbing glass 24 is used to attenuate the heat produced by the lamp 22.

The illumination source 16 further includes an adjustable field aperture 30. The adjustable field aperture 30 allows a user to adjust the area of the printing plate to be tested using the fluorescence dot area meter 10. Preferably, the field aperture 30 can be adjusted from 1 mm to 5 mm using a lever, knob, or other device accessible from the outside of the meter 10.

Figure 3:
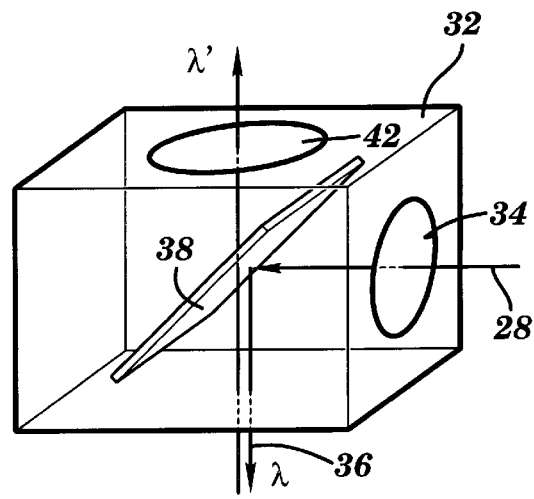
FIG. 3 shows a filter cube assembly for use in the fluorescence dot area meter of the present invention.

The light beam 28 produced by the illumination source 16 is directed into an interchangeable filter cube assembly 32. The filter cube assembly 32 is illustrated in greater detail in FIG. 3. The filter cube assembly 32 includes a first optical filter 34 for filtering the light beam 28 to produce a light beam 36 having a first range of wavelengths. In general, the first optical filter 34 is a short pass filter having a nominal upper cutoff adjusted according to the first range of wavelengths and the type of printing plate 12 to be measured. In the case of the above-described N90™ plate, for example, the first optical filter 34 can be a short pass filter having an upper cutoff of approximately 500 nm, or a bandpass filter having a range of about 450–500 nm.

After being filtered by the first optical filter 34, the light beam 36 is perpendicularly redirected toward the printing plate 12 by a dichroic beam splitter mirror 38. As known in the art, a dichroic beam splitter mirror 38 is designed to reflect light within a first range of wavelengths, and to transmit light within a second, different range of wavelengths. The redirected light beam 36 is subsequently directed against the printing plate 12 through an objective lens assembly 40. A lens shield 41 is coupled to the distal end of the objective lens assembly 40 to eliminate outside light contamination.

The light emitted by the emulsion layer 14 of the printing plate 12 passes through the objective lens assembly 40, through the dichroic beam splitter mirror 38, and through a second optical filter 42. The second optical filter 42 serves to selectively pass only that light λ' having wavelengths corresponding to the light emitted by the emulsion layer 14.

Other light, such as the light λ reflected by the non-emulsion areas of the printing plate, is blocked by the second optical filter 42. For the N90™ plate, for example, the second optical filter 42 can be a long pass filter having a lower cutoff of approximately 540 nm, or a bandpass filter having a range of about 540–640 nm. In general, the second optical filter 42 is a long pass filter having a nominal lower cutoff adjusted according to the wavelengths of the emitted light and the type of printing plate 12 to be measured.

The output of the second optical filter 42 is focused into a light beam 44 by a focusing lens assembly 46, and directed into the sensor 18. Preferably, the sensor 18 comprises a photomultiplier tube (PMT) sensor of a type known in the art. Other types of sensors, such as a silicon diode, a CCD sensor, or the like can also be used without departing from the scope of the present invention. The output of the sensor 18 is passed through an analog-to-digital converter 48 to the processor 20, which calculates dot area on the printing plate 12 in accordance with EQU. 2. The results of the dot area calculation are output to a user via the display 50 of a workstation 52, or on an LCD panel/user interface 53 on the meter 10.

As illustrated in FIG. 2, the illumination source 16 (and associated power source) are preferably enclosed within the main body 54 of the fluorescence dot area meter 10. To increase the portability of the meter 10, however, an external illumination source 55 and/or associated power source can be used. Specifically, as shown in FIG. 4, a fiber optic cable 56 or the like can be used to direct the output of the externally disposed illumination source 55 into the fluorescence dot area meter 10 through the collimator 26 and adjustable field aperture 30. In this manner, the weight of the fluorescence dot area meter 10 can be greatly reduced, allowing a user to easily move the meter 10 by hand over the surface of the printing plate 12.

Figure 7:
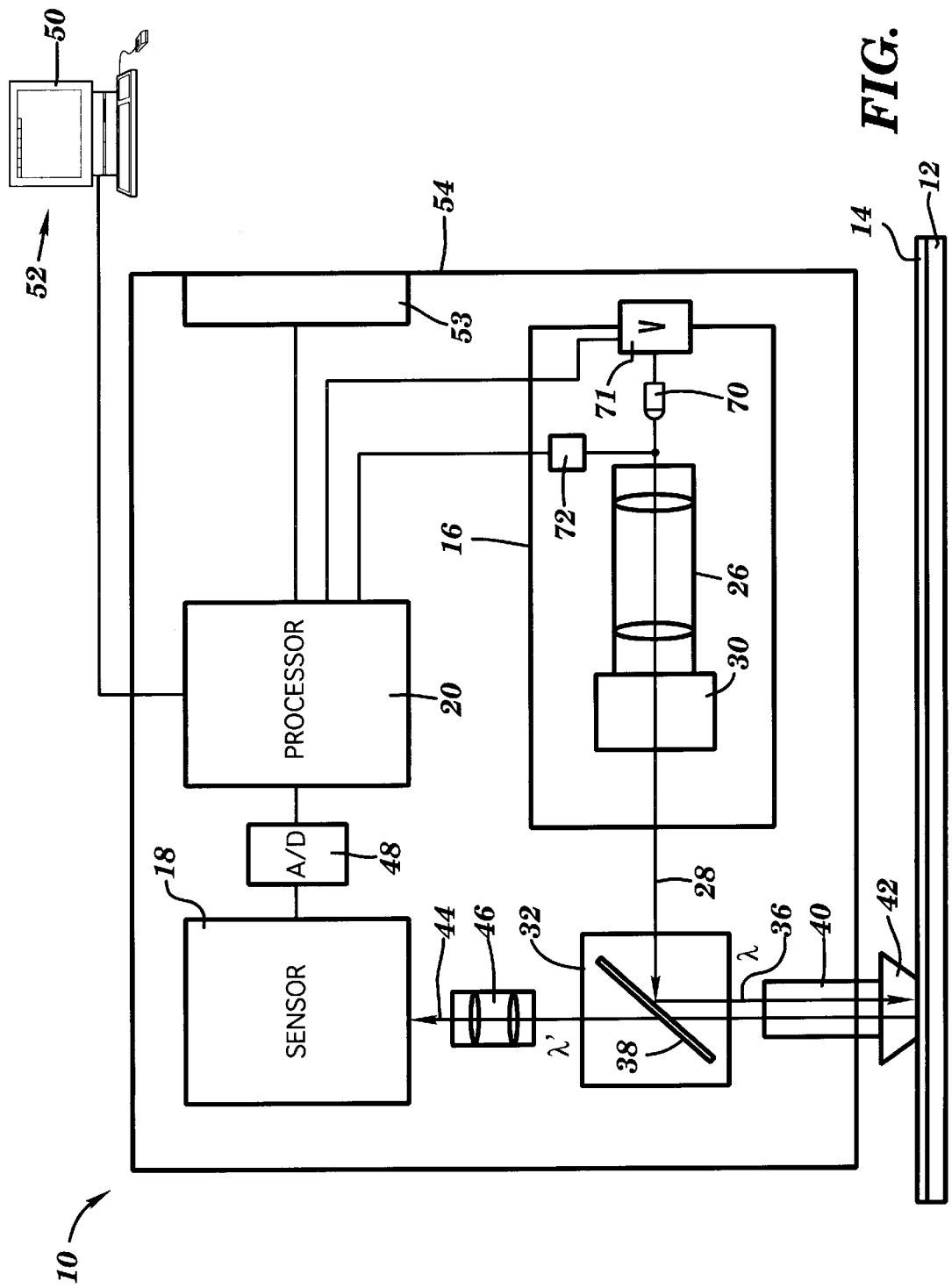
FIG. 7 illustrates an alternate embodiment of a fluorescence dot area meter in accordance with the present invention.

As shown in FIG. 7, a light emitting diode (LED) 70 can be used in lieu of the lamp 22. The LED 70 requires less operating power, reducing the power requirements and cost of the power source of the fluorescence dot area meter 10, and generates much less heat than the lamp 22, eliminating the need for the heat absorbing glass 24. The LED 70 also has a much faster turn-on time, provides a more consistent light output, and is smaller, saving space and weight. Finally, the first optical filter 34 may no longer be required, depending on the range of wavelengths provided by the LED 70, again reducing the cost of the system.

A further improvement to the fluorescence dot area meter 10 is illustrated in FIG. 7. A light integrator 72 is provided to monitor the output of the LED 70, and adjust the length of time the LED 70 is turned on, to ensure that a constant amount of exposure is used for each fluorescence measurement. The output of the light integrator 72 is preferably provided to the processor 20 for analysis and control. The processor 20 controls the power supplied to the LED 70 by the LED power supply 71. For example, if the intensity of the LED 70 lowers as a result of voltage or temperature fluctuations, the processor 20 can regulate the amount of power supplied to the LED 70 by the LED power supply 71, and/or can increase the amount of time the LED 70 is turned on, until the correct amount of light is produced. The performance of the LED 70 can be furnished to a user via the display 50 or the LCD panel/user interface 53.

Figures 5, 6:
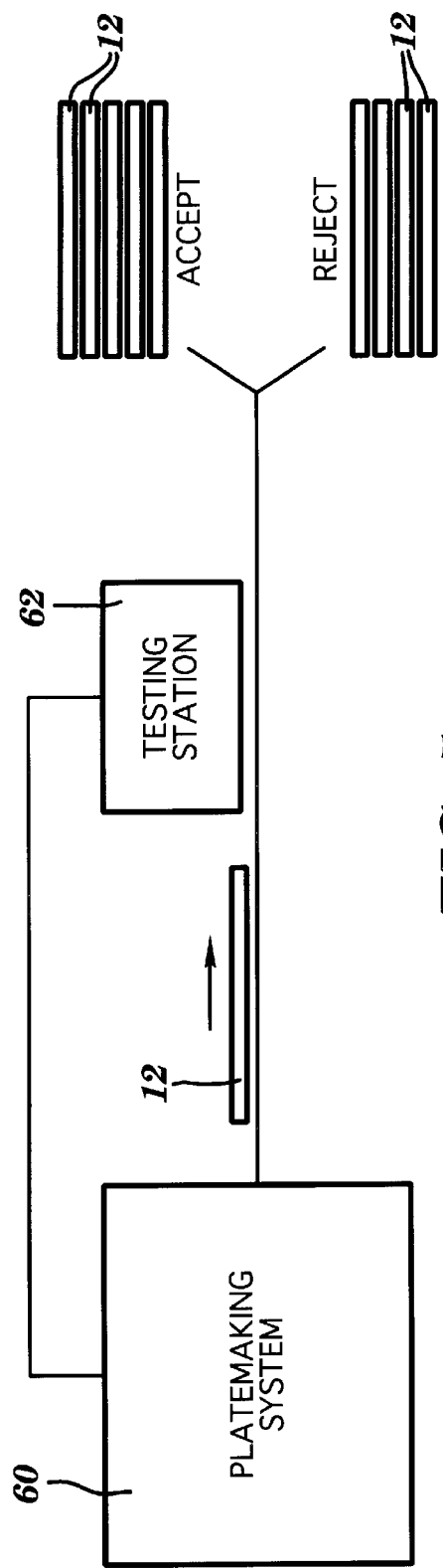
FIG. 5 illustrates a platemaking system incorporating a printing plate testing station, wherein the testing station includes the fluorescence dot area meter of the present invention.
FIG. 6 is a example of a look-up table for use in the testing station of FIG. 5.

The dot area results output by the fluorescence dot area meter 10 are typically used to optimize the performance of a platemaking system. Generally, an operator manually adjusts various platemaking variables in response to the output of the fluorescence dot area meter 10. However, the fluorescence dot area meter 10 can be incorporated into a feedback loop in which the platemaking variables are automatically adjusted according to the type of printing plate 12 being used to optimize the performance of a platemaking system. Such a system is illustrated in FIG. 5.

As each printing plate 12 exits the platemaking system 60, it passes through a testing station 62 including a fluorescence dot area meter 10. The fluorescence dot area meter 10 analyzes at least one predetermined test pattern recorded on a portion of the printing plate 12. The output of the fluorescence dot area meter 10 is subsequently compared to a predetermined "optimum" dot area measurement, and the printing plate 12 is either accepted or rejected according to the result of this comparison. If the printing plate 12 is rejected, the testing station 62 selectively outputs a set of updated platemaking variables, depending upon the output of the fluorescence dot area meter 10 and the type of printing plate 12, to adjust the output quality of the platemaking system 60.

The testing station 62 stores a set of information specific to each type of printing plate 12 output by the platemaking system 60 in a look-up table 64. An example of a look-up table 64 for a printing plate 12 of type "PLATE A" is illustrated in FIG. 6. In this example, the fluorescence dot area meter 10 of the present invention analyzes a 50% test pattern recorded on a portion of the printing plate 12. The output of the fluorescence dot area meter 10 is compared to the % coverage data 66 stored in the look-up table 64. If the output of the meter 10 falls within an acceptable range (49%–51% in this example) the printing plate is accepted. If the output of the meter 10 falls outside of the acceptable range (e.g., $\leq 48\%$, $\geq 52\%$), the printing plate is rejected. In this case, a set of predetermined platemaking variables 68 are provided to the platemaking system 60 to bring the output quality of the system within the acceptable range.

The fluorescence dot area meter 10 of the present invention can also be incorporated into other types of printing systems, such as a "direct to press" printing system. In a direct to press printing system a printing plate is laser imaged after it has been mounted on the printing press. This is in contrast to the more common method used with "direct to plate" systems, where a printing plate is imaged off the press and then mounted to the press by hand. Although direct to press printing systems reduce overall printing time, require less off-line equipment, and reduce errors associated with the registration of multiple printing plates, the problem of image quality measurement using conventional techniques still exists. Advantageously, the present invention can be used to accurately measure the image quality of a printing plate in a direct to press printing system.

Figure 8:
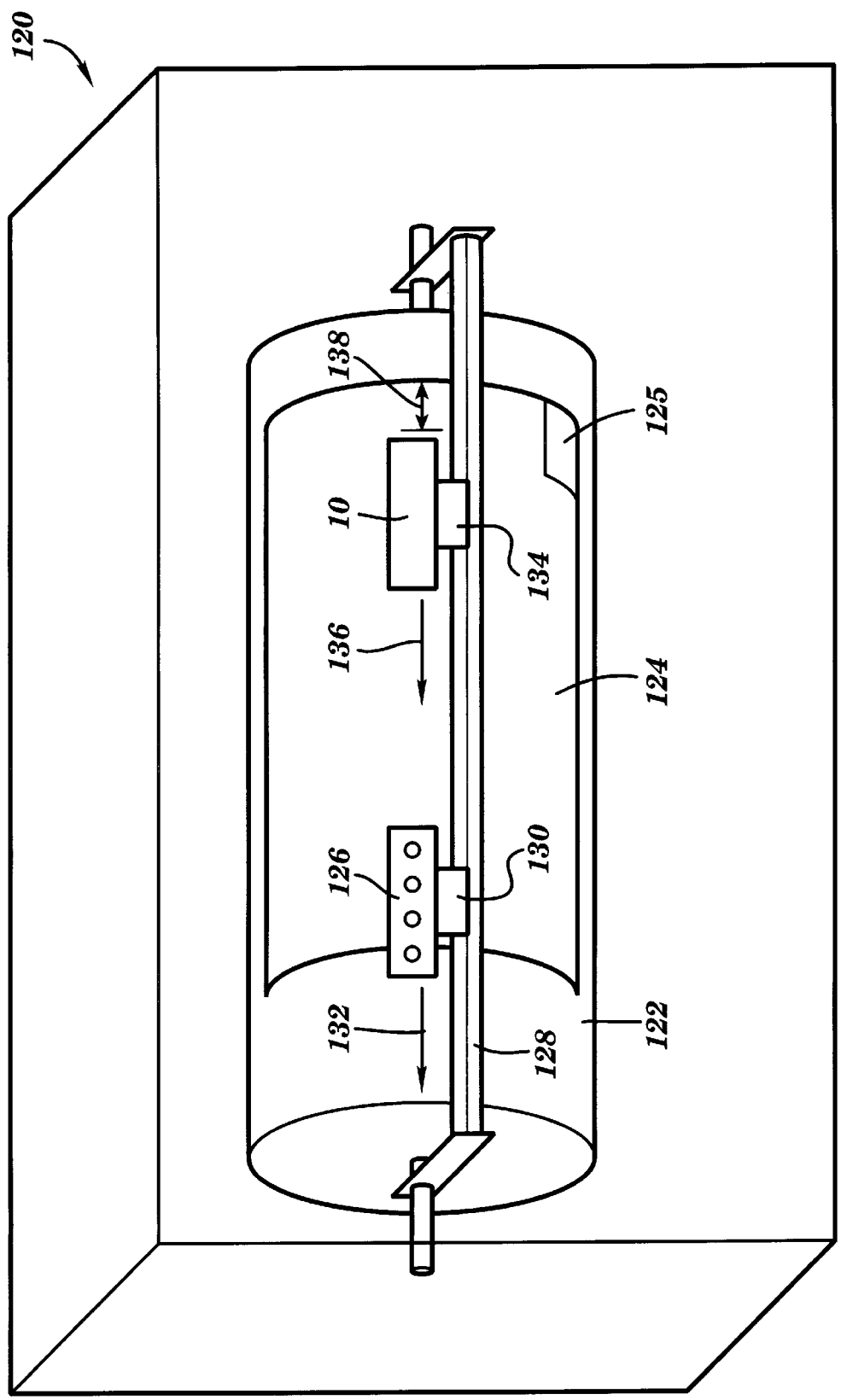
FIG. 8 is a top perspective view of a conventional direct to press printing system incorporating a fluorescence dot area meter in accordance with the present invention.

A conventional direct to press printing system 120 incorporating the fluorescence dot area meter 10 of the present invention is illustrated in FIG. 8. As known in the art, the printing system 120 includes a press cylinder 122 on which an unexposed printing plate 124 is mounted for imaging and subsequent printing. When mounted, the printing plate 124 conforms to the curvature of the press cylinder 122.

A laser imaging head 126 for laser imaging the printing plate 124 is movably mounted on a guide rail 128 which extends across the length of the press cylinder 122. The laser imaging head 126 is driven in a known manner by a drive system 130 along the guide rail 128 as indicated by directional arrow 132 to expose an image on the printing plate 124. The exposure of the image may occur unidirectionally or bidirectionally across the printing plate 124.

As illustrated in FIG. 8, the fluorescence dot area meter 10 is also movably mounted on the guide rail 128. A drive system 134 is provided to displace the fluorescence dot area meter 10 along the guide rail 128 behind the laser imaging head 126 to measure the quality of the image exposed on the printing plate 124 by the laser imaging head 126. This displacement is represented by directional arrow 136 in FIG. 8.

The image quality measurements provided by the fluorescence dot area meter 10 can be used in a feedback loop in a manner similar to that shown in FIG. 5 to optimize the performance of the direct to press printing system 120. Further, the printing plate 124 can be "accepted" or "rejected" based on the measurements provided by the fluorescence dot area meter 10. Alternately, the operating parameters (e.g., exposure) of the laser imaging head 126 can be monitored and adjusted "on the fly" using a test pattern 125 formed adjacent an edge (or other nonimaged or nonprinting portion) of the printing plate 124, allowing the operating parameters to be optimized without having to reimage an entire plate.

In FIG. 8, the fluorescence dot area meter 10 follows the laser imaging head 126 over the entire width of the printing plate 124. In practice, however, the fluorescence dot area meter 10 may only measure a small target area on the printing plate, imaged close to one edge, rather than follow the laser imaging head 126 across the press cylinder 122. In this case, the drive system 134 need only displace the fluorescence dot area meter 10 along a portion of the guide rail 128. This displacement is illustrated in FIG. 8 by directional arrow 138.

Figure 9:
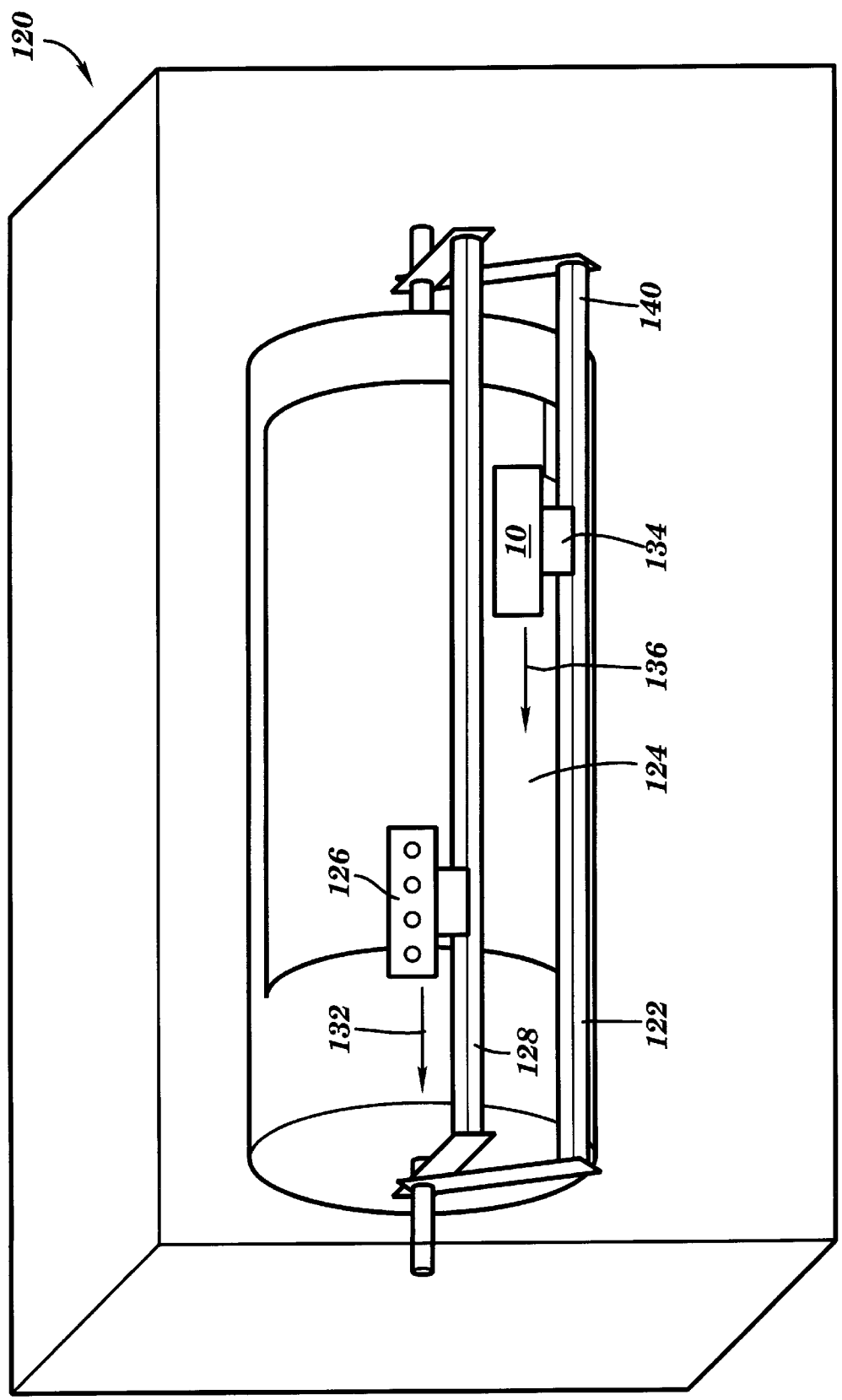
FIGS. 9 and 10 illustrate alternate embodiments of the direct to press printing system of FIG. 7.
Figure 10:
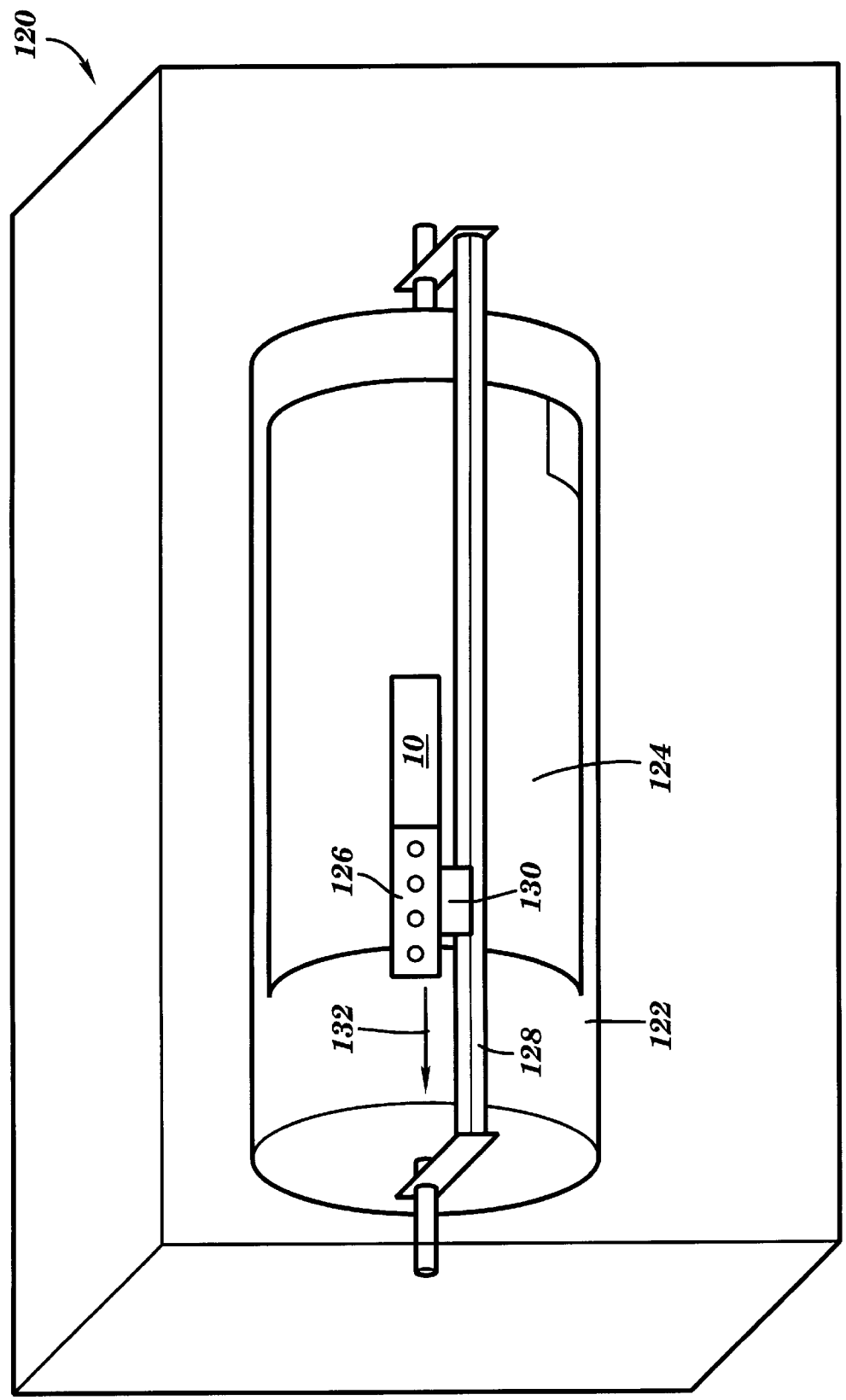

The fluorescence dot area meter 10 and associated drive system 134 may also ride on a separate guide rail 140 as shown in FIG. 9. Alternately, the fluorescence dot area meter 10 may be fixedly secured relative to the press cylinder 122 to measure a predetermined test area on the printing plate. Further, as illustrated in FIG. 10, the fluorescence dot area meter 10 can be attached directly to the laser imaging head 126. In this arrangement, only a single drive system, such as drive system 130, is required to displace the combination of the laser imaging head 126 and fluorescence dot area meter 10 along the guide rail 128.

In an alternate type of direct to press system, the press cylinder 122 is coated directly with an emulsion, obviating the need for the printing plate 124. The emulsion layer is then imaged by the laser imaging head 126 to produce a print image on the press cylinder 122. The fluorescence dot area meter 10 of the present invention may be used to determine halftone dot area on the press cylinder 122 if the emulsion contains a fluorescent compound.

As described above, the fluorescence dot area meter 10 of the present invention uses the fluorescence of the emulsion 14 on a printing plate 12 to accurately measure halftone dot area. Although the meter 10 can be used with many types of currently available printing plates which inherently contain fluorescent compounds, such as the aluminum N90™ printing plate manufactured by the Agfa Division of Bayer Corporation, not all printing plates are capable of fluorescence. However, by adding a suitable fluorescent compound to the emulsion or other layer of a printing plate during or after the manufacture of the plate, most, if not all, printing plates can be used with the present invention. Many commonly available fluorescent dyes (e.g., "laser dyes") or other suitable fluorescent compounds can be used to add fluorescence to the emulsion or other layer of a printing plate.

Figure 11:
FIG. 11 is a cross-sectional view of a first embodiment of a printing plate manufactured for use with the fluorescence dot area meter of the present invention.

An example of a printing plate 150 manufactured to fluoresce when irradiated by the fluorescence dot area meter 10 is illustrated in FIG. 11. The printing plate 150 includes a substrate 152 which can be formed of a material such as aluminum or polyester, an intermediate sublayer 154 containing a fluorescent compound, and an emulsion layer 156.

Figure 12:
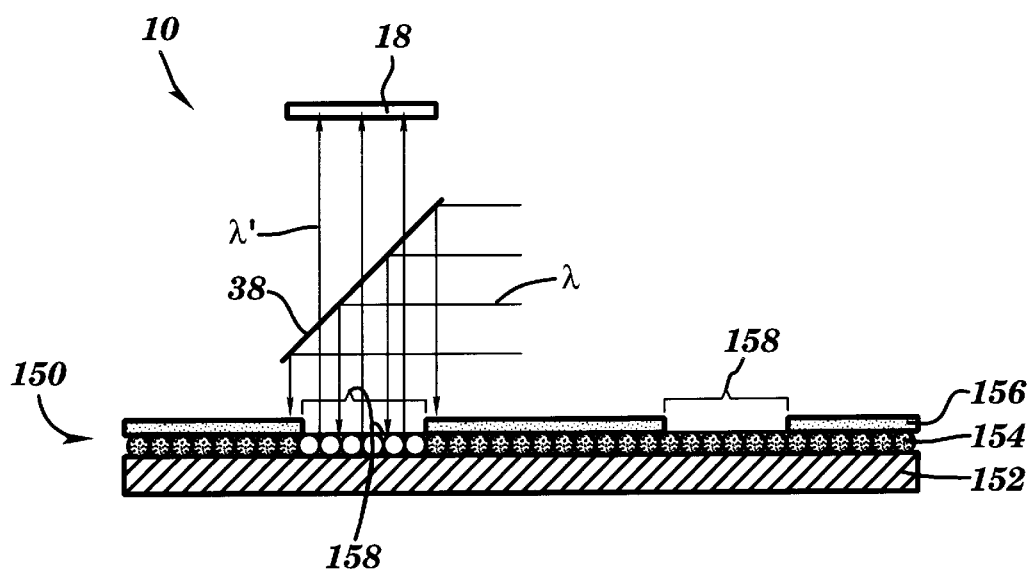
FIG. 12 illustrates the dot area measurement of the printing plate of FIG. 11.

When an imaging laser exposes the printing plate 150, portions of the emulsion layer 156 are removed revealing the underlying sublayer 154. The image quality of the exposed plate 150 may be measured by the fluorescence dot area meter 10 as illustrated in FIG. 12. As shown, the exposed areas 158 of the sublayer 154 fluoresce when illuminated by light having a first range of wavelengths $\lambda$, emitting light within a second, higher range of wavelengths $\lambda'$ which is detected by sensor 18.

Figure 13:
FIG. 13 is a cross-sectional view of a second embodiment of a printing plate manufactured for use with a fluorescence dot area meter of the present invention.

A printing plate may also be manufactured to optimize the performance of a fluorescence dot area meter 10 which uses an LED for illumination (e.g., FIG. 7). Such a printing plate 160 is illustrated in FIG. 13. Of course, the image quality on the printing plate 160 can also be accurately measured using any of the previously described embodiments of the fluorescence dot area meter 10.

The printing plate 160 includes a substrate 162 formed of aluminum, polyester, or other suitable material, an intermediate sublayer 164 containing a first fluorescent compound, and an emulsion layer 166 containing a second fluorescent compound. When illuminated by light having a range of wavelengths $\lambda$, the first fluorescent compound emits light within a first range of wavelengths $\lambda_1'$, while the second fluorescent compound emits light within a second, range of wavelengths $\lambda_2'$.

Figure 14:
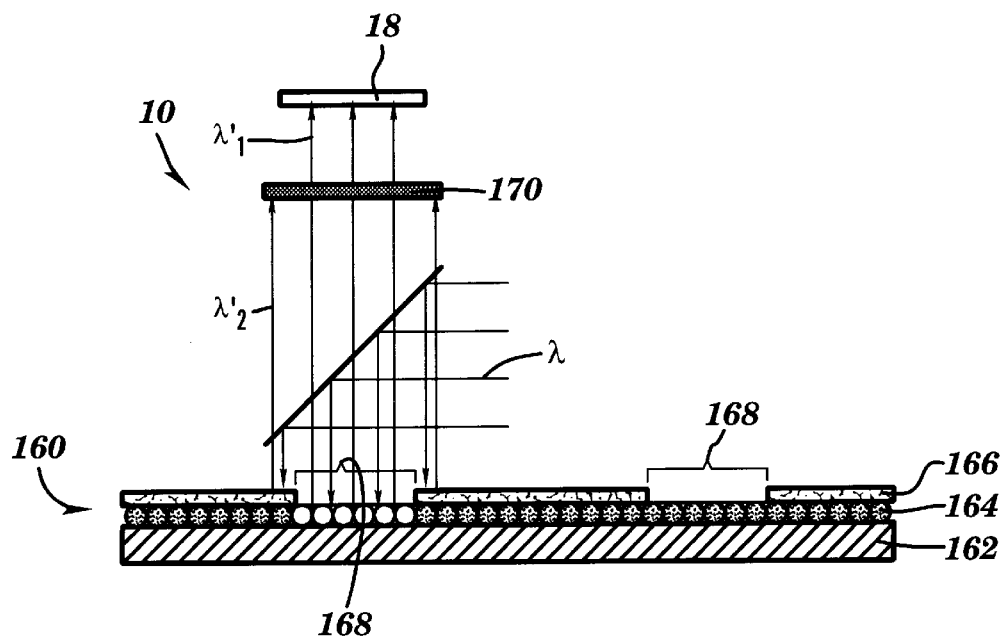
FIG. 14 illustrates the dot area measurement of the printing plate of FIG. 13.

After laser imaging, selected portions of the emulsion layer 166 are removed, revealing areas 168 of the sublayer 164. This is illustrated in FIG. 14. The exposed areas 168 of the sublayer 164 emit light within a first range of wavelengths $\lambda_1'$ when illuminated by light having a range of wavelengths $\lambda$. At the same time, the remaining portions of the emulsion layer 166 emit light within a second range of wavelengths $\lambda_2'$. The light $\lambda_1'$ (or $\lambda_2'$) can then be isolated using appropriate filtering 170 and detected by the sensor 18.

A green LED is preferably used for illumination to optimize the efficiency and the signal to noise ratio of the fluorescent dot area meter 10. The choice of a green LED is based in part on the fact that many sensors suitable for use in the flouorescent dot area meter 10 of the present invention are typically more sensitive to longer wavelengths (e.g., red or infrared). To take advantage of this effect, the first fluorescent compound in the sublayer 164 of the printing plate 160 is chosen such that it will fluoresce red or infrared when illuminated by the green LED. The second fluorescent compound in the emulsion layer 166 is chosen such that it will not fluoresce, or will fluoresce at a lower wavelength (e.g., yellow), when illuminated by the green LED.

The foregoing description of the present invention has been presented for purposes of illustration and description. It is not intended to be exhaustive or to limit the invention to the precise form disclosed, and many modifications and variations are possible in light of the above teaching. Such modifications and variations that may be apparent to a person skilled in the art are intended to be included within the scope of this invention as defined by the accompanying claims.

We claim:

1. A printing system comprising:
   a press cylinder;
   a printing plate mounted on the press cylinder;
   a system for exposing an image on the printing plate; and
   an apparatus for measuring halftone dot area on the printing plate while the printing plate is mounted on the press cylinder, the measuring apparatus including an illumination source for illuminating the printing plate with light having a first range of wavelengths, a system for detecting light, emitted by the printing plate, within a second, higher range of wavelengths, and a system for determining halftone dot area based on the emitted light detected by the light detecting system.

2. The printing system according to claim 1, wherein the illumination source includes a light source and a filter system for filtering an output of the light source to provide light having the first range of wavelengths.

3. The printing system according to claim 1, wherein the light detecting system includes a filter system for isolating the light emitted by the printing plate.

4. The printing system according to claim 1, wherein the printing plate includes a layer containing at least one fluorescent compound, and wherein the layer emits light within the second, higher range of wavelengths when illuminated by the light having the first range of wavelengths.

5. The printing system according to claim 1, wherein the illumination source includes a light emitting diode (LED) for illuminating the printing plate.

6. The printing system according to claim 1, wherein the illumination source further includes:
   an illumination controller for regulating an illumination output of the illumination source.

7. The printing system according to claim 1 further including:
   an apparatus for selectively accepting or rejecting the printing plate after exposure based on the halftone dot area measurement provided by the measuring apparatus.

8. The printing system according to claim 1, wherein the printing plate includes a test pattern, and wherein the printing system further includes:
   an apparatus for selectively adjusting at least one operating parameter of the image exposing system based on at least one halftone dot area measurement of the test pattern by the measuring apparatus.

9. A printing system comprising:
   a press cylinder;
   an imageable material disposed on the press cylinder;
   a system for exposing an image on the imageable material; and
   an apparatus for measuring halftone dot area on the imageable material while the imageable material is mounted on the press cylinder, the measuring apparatus including an illumination source for illuminating the imageable material with light having a first range of wavelengths, a system for detecting light, emitted by the imageable material, within a second, higher range of wavelengths, and a system for determining halftone dot area based on the emitted light detected by the light detecting system.

10. The printing system according to claim 9, wherein the imageable material includes at least one layer containing at least one fluorescent compound.

11. A printing method comprising the steps of:
    mounting a printing plate on a press cylinder;
    exposing an image on the printing plate; and
    measuring halftone dot area on the printing plate while the printing plate is mounted on the press cylinder, the measuring step including the steps of illuminating the printing plate with light having a first range of wavelengths, sensing light emitted by the printing plate within a second, higher range of wavelengths, and determining halftone dot area based on the light emitted by the printing plate.

12. The method of claim 11, further including the step of:
    providing the printing plate with at least one layer containing at least one fluorescent compound.

13. A printing system comprising:
    a press cylinder;
    an imageable material disposed on the press cylinder;
    an arrangement for exposing an image on the imageable material;
    an apparatus for measuring halftone dot area on the imageable material while the imageable material is disposed on said press cylinder, including a system for determining halftone dot area based on:

$$\% = \frac{(t-p)^N}{(s-p)^N} \times 100$$

where
%=a percent area covered by halftone dots
t=density of a halftone tint area
p=density of a background area
s=density of a solid area
N=correction factor for optical effects.

* * * * *